United States Patent [19]

Manning

[11] Patent Number: 5,541,335
[45] Date of Patent: Jul. 30, 1996

[54] PROCESS FOR PREPARING NIZATIDINE

[75] Inventor: Hartford W. Manning, Aurora, Canada

[73] Assignee: Torcan Chemical Ltd., Aurora, Canada

[21] Appl. No.: 272,459

[22] Filed: Jul. 11, 1994

[51] Int. Cl.$^6$ ............................................. C07D 277/28
[52] U.S. Cl. ............................................. 548/205
[58] Field of Search ............................................. 548/205

[56] References Cited

U.S. PATENT DOCUMENTS 4,375,547  3/1983  Pioch ............................................. 548/205

FOREIGN PATENT DOCUMENTS 8604449  4/1985  Brazil .

OTHER PUBLICATIONS

"Replacement of Alcoholic Hydroxyl Groups By Halogens and Other Nucleophiles via Oxyphosphonium Intermediates" Org. Reactions 29, 1–162 (1983).

"A Novel Method For Synthesis of Unsymmetrical Secondary and Tertiary Amines From Reactions of Alcohols With Amines By Utilizing Aminophosphonium Salts", Tetrahedron Letters No. 7, pp. 471–471, 1975 Pergamon Press, U.K.

No. 738—"Sels d'alcoyloxyphosphonium", Bulletin de la Societe Chimique de Fr ance 1971 No. 12 pp. 4368–4373.

Katritzky, Comprehensive Heterocyclic Chemistry vol. 6 p. 277 (1984).

*Primary Examiner*—Robert Gerstl
*Attorney, Agent, or Firm*—Ridout & Maybee

[57] ABSTRACT

Nizatidine is prepared by a process in which the final step is the reaction of the 2-hydroxymethyl analog of nizatidine, namely N-[2-[[[2-(hydroxymethyl)-4-thiazolidyl]-methyl]thio]ethyl]-N'-methyl-2-nitro-1,1-ethenediamine, with excess dimethylamine and an (N,N-dimethylamino)phosphonium halide such as (N,N-dimethylamino)triphenylphosphonium bromide. The process yields nizatidine in a very high state of purity.

9 Claims, No Drawings

PROCESS FOR PREPARING NIZATIDINE

FIELD OF THE INVENTION

This invention relates to the pharmaceutical nizatidine, and more particularly to processes for the synthesis of nizatidine, and novel intermediates in such synthesis.

BACKGROUND OF THE INVENTION

Nizatidine, the systematic chemical name of which is N-[2-[[[2-(dimethylaminomethyl)-4-thiazolyl]methyl]thio]ethyl]-N'-methyl-2-nitro-1,1-ethenediamine, and which has the formula (I):

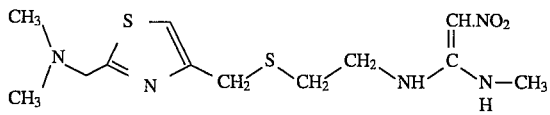

is known compound, effective as a histamine H2 receptor antagonist, and useful in the treatment of peptic ulcers. The compound and a method for its preparation are described in U.S. Pat. No. 4,375,547 Pioch, to Eli Lilly and Co.

A commercially attractive process for producing pharmaceuticals such as nizatidine should yield the product in a highly pure form, or at least in an easily purifiable form. This is particularly advantageous for the last step in a pharmaceutical product synthesis. If the recovery and purification of the product to the high standards required of a pharmaceutical are difficult and expensive to achieve, the process may not be economically viable.

The Bronsted basicity of nizatidine, i.e. its basicity towards protons, derives essentially from the dimethyl amino group on the thiazole ring acting in concert with the nitrogen of the thiazole ring. If, therefore, in the final synthetic step in making nizatidine there can be created a precursor which is much more weakly basic than nizatidine, then the separation of nizatidine from the precursor and other by-products derived from the precursor can be achieved by a simple acid-base extraction. This will constitute a rugged (in the sense of readily scaled-up, insensitive to parameter variable) but simple procedure for obtaining very pure pharmaceutical product which is industrially applicable.

In Canadian Patent 1,263,400 Alhede et al (Gea), there is disclosed a process for making ranitidine. Nizatidine is often compared with ranitidine, a compound having a similar pharmaceutical activity and chemical structure, differing chemically from nizatidine, inter alia, in the presence of a furan ring system in place of the thiazole ring system of nizatidine. The Alhede et al synthesis of ranitidine involves as a final step replacement of a benzylic type hydroxyl by the dimethylamino function. Use of elevated temperatures and closed pressure vessels are reported to be required. There is no description of the benefits of this procedure for obtaining high quality product by simple extraction, nor that it might be applicable to any other product preparation besides ranitidine. Methods of chemical synthesis of ranitidine cannot predictably be applied to the synthesis of nizatidine, because of the differences in resonance and inductive effects introduced by the furan ring system as compared with the thiazole ring system.

It is an object of the present invention to provide a novel method for the synthesis of nizatidine.

It is a further object of the present invention to provide novel intermediates useful in such a synthesis.

SUMMARY OF THE INVENTION

The present invention provides a process for the preparation of nizatidine in which, as one of the final steps, an intermediate compound which has a hydroxymethyl substituent at the 2-position of the thiazole ring, in the presence of excess dimethylamine, is treated with at least a stoichiometric amount of a phosphonium reagent corresponding to the formula:

in which L represents dimethylamino, aryl lower alkyl amino, phenyl, alkylcarboxy substituted phenyl, lower alkyl or aryloxy, and X represents bromine or chlorine. The phosphonium reagent can be added to the reaction mixture as such, or formed in situ.

The replacement of the hydroxy group on the 2-methyl substituent on the thiazole ring with an amino group, as the last step in the nizatidine synthesis, using the phosphonium reagents of the process of the invention, greatly increases the basicity of the compound. While it is not intended that the invention should be limited to any particular theory or mode of action, it appears that, when the hydroxy group is present on the 2-methyl group, it forms a hydrogen bond with the ring amino group, which reduces the basicity of the compound. Replacement of the hydroxyl group with an amino group, as in the present invention, substantially increases the basicity of the desired compound, rendering its recovery in high purity, based on its basic properties in comparison with the acidity of the by-products, a relatively simple procedure. Thus the inclusion of such a step as the final synthetic step, instead of elaborating the 4-thioethyl substituent chain as the final steps in a nizatidine synthesis, provides an improved process for obtaining nizatidine in high purity.

DESCRIPTION OF THE PREFERRED EMBODIMENTS

The term "alkyl" is used herein generally refers to alkyl groups, straight chain or branched, having up to 8 carbon atoms. "Lower alkyl" refers to such groups having 1–4 carbon atoms. "Aryl" refers to aromatic cyclic radicals of 6–10 nuclear carbon atoms.

One specific example of a preferred reagent (II) for use in the process of the present invention is the complex of tris(dimethylamino)phosphine and carbon tetrachloride. It can be prepared in situ by reaction of technical 85% tris(dimethylamino) phosphine [hexamethylphosphorus triamide] with a mixture of carbon tetrachloride and excess dimethylamine in dimethylformamide solvent. (N,N-dimethyl-amino)triphenylphosphonium bromide is another preferred reagent. This is a known compound. It can also, if desired, be prepared in situ by reaction of bromotriphenylphosphonium bromide with dimethylamine, in dimethylformamide solvent. Analogous compounds to (N,N-dimethylamino) triphenylphosphonium bromide, e.g. those where the phenyl groups carry acidic substituents such as hydrolyzable ester groups, are also suitable and preferred. In general, the phosphonium halide compound is one which provides a leaving group which does not compete with the dimethylamine, in its reaction with hydroxymethyl. Choice of L to be dimethylamino in the formula II above is thus preferred, but other choices within the scope set out above are suitable. Best yields are obtained from choice of compounds II in which L is dimethylamino and X is chlorine.

When the phosphonium reagent is pre-prepared, it should be added to the reaction mixture last. When it is formed in situ as is generally preferred, such formation should take place last. This is because the phosphonium reagent reacts with the hydroxy group of the hydroxymethyl as soon as it is created.

The process of reaction with the dimethylamine to form nizatidine is suitably conducted in solution in a dry polar organic solvent, most preferably dimethylformamide or dimethylacetamide. The temperature of the reaction is not critical, but low temperatures tend to mot selective, cleaner reactions. For the most preferred reagents, temperatures from about −40° to +30° C. are suitable, e.g. room temperatures. Elevated temperatures of 90° C. and the like, and the use of closed pressure vessels, as reported for the ranitidine process in the aforementioned Gea patent, are unnecessary and undesirable. From 1–3 equivalents of the phosphonium halide reagent are suitably used relative to the nizatidine precursor, and preferably at least 10 equivalents of free dimethylamine on the same basis, although this is not critical as long as there is a substantial excess. Excess dimethylamine should be present throughout the addition or formation of the phosphonium halide reagent. The reaction is preferably conducted under an inert atmosphere which effectively excludes moisture.

The recovery of the nizatidine product from the reaction mixture is simply accomplished by acidification and solvent extraction of the non-basic materials under acidic conditions, followed by basification and solvent extraction of the nizatidine product under basic conditions.

The intermediate product for reaction with the phosphonium bromide reagent, N-[2-[[2-(hydroxymethyl)-4-thiazolyl]-methyl]thio]ethyl]-N'-methyl-2 -nitro-1,1-ethenediamine, of formula:

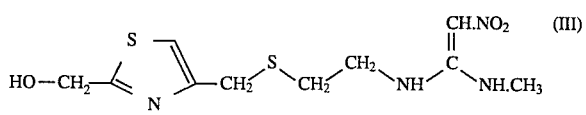

is a novel compound, and constitutes another aspect of the present invention. It can be prepared by reacting 4-[[(2-aminoethyl)thio]methyl]-2-hydroxymethylthiazole, of formula:

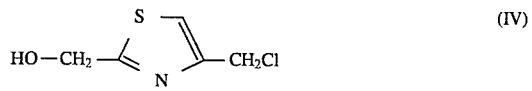

itself preparable by reaction of 4-chloromethyl-2-hydromethylthiazole with cysteamine hydrochloride, followed by 2-methylamino-2-methylthio-1-nitroethylene. The compound 4-chloromethyl-2-hydroxymethylthiazole is also novel and forms an aspect of the present invention. It can be prepared by acid hydrolysis of the corresponding 2-acetoxymethyl compound.

In addition, the compounds 4-[[(2-aminoethyl)thio]methyl]-2-hydroxymethylthiazole, and 2-acetoxymethyl-4-chloromethyl-4-hydroxythiazoline, are novel compounds, and constitute further aspects of this invention.

The invention is further described for illustrative purposes in the following examples, which describe a sequential, seven-step process for preparing nizatidine in accordance with the invention, and starting with the common reagents sodium acetate, 2-chloroacetonitrile, hydrogen sulfide and dichloroacetone.

SPECIFIC DESCRIPTION OF THE MOST PREFERRED EMBODIMENTS

EXAMPLE 1

To 75.0 g of sodium acetate and 69.0 g of 2-chloroacetonitrile in 58 ml of 1,2-dichloroethane and 125 ml of water was added 14.74 g of tetrabutlyammonium bromide and the two phase mixture was heated and stirred at reflux for 18 hours. The mixture was cooled to room temperature and filtered to remove a small amount of solid. The two layers were separated and the organic phase washed with water and dried over magnesium sulfate and concentrated by distilling the organic solvent through a Vigreux column. The residue was distilled under a water aspirator vacuum and the fraction boiling at 75°–85° C. collected. The yield of 2-acetoxyacetonitrile was 75.95 g (84%).

EXAMPLE 2

Into a solution of 75.95 g of 2-acetoxyacetonitrile prepared according to Example 1, in 2.3 L of ethanol and 7.76 g of triethylamine, was bubbled hydrogen sulfide gas for a period of 2 hours while maintaining a temperature of 0° C. The solution was then stirred overnight at room temperature. The solution was then placed under reduced pressure for 1 hour to strip out the bulk of residual gas and then was distilled under reduced pressure to remove ethanol at a bath temperature of <=80° C. The residue (81.9 g) represents 80% yield of 2-acetoxythioacetamide.

EXAMPLE 3

A mixture of 5.33 g of 2-acetoxythioacetamide, prepared according to Example 2, 5.21 g of 1,3-dichloroacetone, 3.44 g of sodium bicarbonate and 20 ml of 1,2-dichloroethane was heated at 40° C. for 15 hours. The mixture was filtered to remove insoluble inorganics and concentrated under reduced pressure to an oil. The oil was taken up in 25 ml of isopropyl alcohol saturated with hydrogen chloride (5N) and 25 ml of isopropanol added to improve stirring. The slurry was stirred for 30 minutes at 0° C. and then filtered. The precipitate was washed with cold IPA and dried at room temperature under reduced pressure. The product 2-acetoxymethyl-4-chloromethyl-4-hydroxythiazoline hydrochloride was obtained in 60% yield (1.66 g).

EXAMPLE 4

A mixture of 5.33 g of 2-acetoxythioacetamide prepared according to Example 2, 5.21 g of 1,3-dichloroacetone, 6.88 g of sodium bicarbonate and 20 ml of 1,2-dichloroethane was stirred at room temperature for 87 hours. The mixture was filtered to remove insoluble inorganics and concentrated under reduced pressure to an oil. The oil was taken up in 4 mls of 1,2-dichloroethane and 25 mls of cyclohexane added dropwise. The slurry was stirred for 1 hour at 0° C. and then filtered. The precipitate was washed with cyclohexane and dried at room temperature under reduced pressure. The product, 2-acetoxymethyl-4-chloromethyl-4-hydroxy-thiazoline was obtained in 92% yield (8.25 g).

EXAMPLE 5

7.48 g of 2-acetoxymethyl-4-chloromethyl-4-hydroxythiazoline, prepared according to either Example 3 or 4, was suspended in 20 ml of 5N hydrogen chloride in isopropanol and heated to reflux for 45 minutes. The suspension was cooled in an ice bath and 30 ml of diethyl ether added dropwise over 30 minutes. The slurry was stirred a further 30 minutes at 0° C. and the precipitate filtered, washed with ether and dried under vacuum. 4-chloromethyl-2-hydroxymethylthiazole hydrochloride, 6.22 g (93% yield) was obtained.

EXAMPLE 6

To a suspension of 1.0 g of 4-chloromethyl-2-hydroxymethylthiazole hydrochloride, prepared according to Example 5, and 0.74 g of cystamine hydrochloride in 10 ml of dichloromethane at room temperature was added dropwise 1.6 of triethylamine. The mixture warmed slightly. The reaction mixture was stirred at room temperature for 3.5 hours. No starting material was detected by HPLC. Then 1.04 g of 2-methylamino-2-methylthio-1-nitroethylene was added followed by 0.71 g of triethylamine. The slurry was heated to reflux in an oil bath at 40° C. for 11 hours. To the cooled mixture 10 ml of water was added and the heterogeneous mixture extracted five times with 100 ml of methylene chloride and three times with 50 ml of 20/80 v/v methanol/methylene chloride. The combined extracts were concentrated to give a residue which was chromatographed on silica eluting with 20–25% methanol in ethyl acetate to give a clean fraction identified as N-[2-[[[2-(hydroxymethyl)-4-thiazolyl]-methyl]thio]ethyl]-N'-methyl-2-nitro-1,1-ethenediamine.

EXAMPLE 7

Potassium hydroxide (10.6 g) was added to a suspension of 6.82 g of cysteamine hydrochloride and 10.0 g of 4-chloromethyl-2-hydroxymethylthiazole hydrochloride in 100 ml isopropanol. The resulting suspension was stirred an room temperature for 2 hours and filtered through a pad of celite to remove insoluble inorganics and concentrated under reduced pressure. The residue was taken up in dichloromethane and filtered through a pad of celite and concentrated under reduced pressure. The oil (12.54 g) represents a quantitative yield of 4-[[(2-aminoethyl)thio]methyl]-2-hydroxymethylthiazole contaminated only with inorganic salts.

EXAMPLE 8

14.11 g of 2-methylamino-2-methylthio-1-nitroethylene was added to a solution of 15.81 g of 4-[[(2-aminoethyl)thio]-methyl]-2-hydroxymethylthiazole in 190 ml of DMF. The solution was stirred at room temperature for 4 days. The reaction mixture was concentrated under reduced pressure to give a residue which was chromatographed on silica gel eluting with 5–10% methanol in acetonitrile to give 12.8 g (61%) of N-[2-[[[2-(hydroxymethyl)-4-thiazolyl]methyl]thio]ethyl]-N'-methyl-2-nitro-1,1 -ethenediamine.

EXAMPLE 9

1.5 ml of a 2.87N solution of dimethylamine in dimethylformamide was added to 236 mg of bromotriphenylphosphonium bromide ($Ph_3PBr^+Br^-$) and the solution stirred at room temperature for 10 minutes under nitrogen. This formed (N,N-dimethylamino)-triphenylphosphonium bromide in situ. N-[2-[[[2-(hydroxymethyl)-4-thiazolidyl]-methyl]thio]ethyl]-N'-methyl-2-nitro- 1,1-ethenediamine prepared according to Example 6, (56.8 mh) in 1.5 ml of the dimethylamine/DMF solution was added and the combination stirred and heated for 15 hours in a glass pressure tube at 90°–95° C. The reaction mixture was cooled, transferred to a round bottomed flask, and concentrated under vacuum. The nonvolatile residue was taken up in a 20% brine solution and made acidic with 6N hydrochloric acid. The solution was extracted twice with small portions of dichloromethane to remove non-basic materials. The aqueous phase was then basified to pH 11 with 50% aqueous sodium hydroxide and extracted four times with 50 ml of dichloromethane. The combined extracts were evaporated to dryness. The residue was identified by HPLC retention time and proton NMR as being essentially pure N-[2-[[[2-(dimethylaminomethyl)-4-thiazolyl]methyl]thio]ethyl]-N'-methyl-2 -nitro-1,1-ethenediamine.

EXAMPLE 10

A solution of 1.76 mls of 85% hexamethylphosphorus triamide in 3.5 ml pyridine was added dropwise over 25 mins. to a cold (–40° C.) solution of 1.00 g of N-[2-[[[2-(hydroxymethyl)-4-thiazolyl]methyl]thio]-ethyl]-N'-methyl-2-nitro-1,1-ethenediamine in 8 ml of DMF, 1.0 ml of carbon tetrachloride and 2.5 ml (1.7 g) of dimethylamine. The resulting solution was stirred at –40° C. for 1 hour before being quenched with water. The mixture was made basic with 50% potassium hydroxide and extracted four times with 25 ml of dichloromethane. The combined extracts were washed with brine, dried ($MgSO_4$) and evaporated to dryness. The residue was taken up in 4 mls of methyl ethyl ketone and cooled to 0° C. Crystallization of 0.18 gm of product occurred. Mother liquors were concentrated and chromatographed over silica gel, eluting with 35% methanol/ethyl acetate, to obtain a further 0.58 gm, for a total yield of 70% of N-[2[[[2-dimethylaminomethyl)-4-thiazolyl]methyl]thio]ethyl]-N'-methyl-2-nitro-1,1-ethenediamine.

I claim:

1. A process for preparing N-[2-[[[2-(dimethylaminoethyl)-4-thiazolyl]-methyl]thio]ethyl]-N'-methyl-2-nitro-1,1-ethenediamine (nizatidine) of formula:

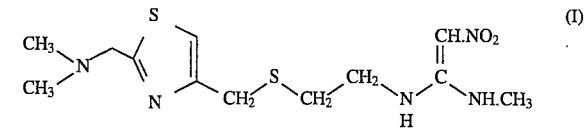

which comprises reacting an N,N-dimethylamino-phosphonium halide of the general formula:

in which L represents dimethylamino, aryl lower alkyl amino, lower alkyl or aryloxy, and X represents bromine or chlorine, with N-[2-[[[2-(hydroxymethyl)-4-thiazolyl]-methyl]thio]ethyl]-N'-methyl-2-nitro-1,1-ethenediamine, in the presence of excess dimethylamine, at a temperature in the range of from about –40° C. to 30° C., and recovering the nizatidine so formed.

2. The process of claim 1 wherein the dimethylamine is present in the reaction mixture in excess, at the time the compound of formula II is added to the reaction mixture or is generated in the reaction mixture.

3. The process of claim 1, wherein the N,N-dimethylamino-phosphonium halide is generated in situ.

4. The process of claim 2 wherein the reaction is conducted in a dry polar organic solvent.

5. The process of claim 4 wherein the solvent is dimethylformamide or dimethylacetamide.

6. The process of claim 2 wherein L in the reagent of formula (II) is dimethylamino.

7. The process of claim 1 wherein the N-[2-[[[2-(hydroxymethyl)-4-thiazolyl]methyl]thio]ethyl]-N'-methyl-2-nitro-1,1-ethenediamine is prepared by reaction of 2-methylamino-2-methylthio-1-nitroethylene with 4-[[(2-aminoethyl)thio]methyl]-2-hydroxymethyl thiazole.

8. The process of claim 7 wherein the 4-[[(2-aminoethyl)thio]methyl]-2-hydroxymethyl thiazole is prepared by reacting 4-chloromethyl-2-hydroxymethylthiazole or an addition salt thereof or a 2-acetoxy analog thereof with cysteamine hydrochloride.

9. A process of preparing N-[2-[[2-(dimethylaminoethyl)-4-thiazolyl]-methyl]thio]ethyl]-N'-methyl-2-nitro-1,1-ethenediamine (nizatidine) which comprises reacting hexamethylphosphorus triamide with a solution of N-[2-[[[2-(hydroxymethyl)-4-thiazolyl]methyl]thio]-ethyl]-N'-methyl-2-nitro-1,1-ethenediamine, carbon tetrachloride and excess dimethylamine, at a temperature in the range from about −40° C. to 30° C.

* * * * *